United States Patent [19]

Lee et al.

[11] Patent Number: 5,571,523

[45] Date of Patent: Nov. 5, 1996

[54] ANTIOXIDANT-INDUCED APOPTOSIS IN VASCULAR SMOOTH MUSCLE CELLS

[75] Inventors: Mu-En Lee, Newton, Mass.; Edgar Haber, Salisbury, N.H.; Jer-Chia Tsai, Kaohsiung, Taiwan

[73] Assignee: President and Fellows of Harvard College, Cambridge, Mass.

[21] Appl. No.: 401,341

[22] Filed: Mar. 9, 1995

[51] Int. Cl.⁶ ..................................................... A61F 2/02
[52] U.S. Cl. ................................................................ 424/423
[58] Field of Search ............................................... 424/423

[56] References Cited

U.S. PATENT DOCUMENTS 5,464,833  11/1995  Nakai et al. ............................. 514/251

OTHER PUBLICATIONS

Abello et al., "Antioxidants Modulate Induction of Programmed Endothelial Cell Death (Apoptosis) by Endotoxin", 1994, Arch. Surg., 129:134–41.

Garcia et al., "Prevention of Programmed Cell Death of Sympathetic Neurons by the bcl–2 Proto–Oncogene," 1992, Science, vol. 258.

Gavrieli et al., "Identification of Programmed Cell Death In Situ via Specific Labeling of Nuclear DNA Fragmentation," 1992, J. Cell Biology, 119:(3):493–501.

Gerschenson et al., "Apoptosis: A Different Type Of Cell Death," Apr. 1992, Faseb J., 6:2450.

Hockenberry et al., "BCL2 Protein Is Topographically Restricted in Tissues Characterized By Apoptotic Cell Death," 1991, Cell Biology, 88:6961–6965.

Jacobson et al., "Bcl–2 blocks apoptosis in cells lacking mitochondrial DNA," 1993, Nature, vol. 361.

Kane et al., "Bcl–2 Inhibition of Neural Death: Decreased Generation of Reactive Oxygen Species," 1993, Science, vol. 262.

Louis et al., "CMTF Protection of Oligodendrocytes Against Natural and Tumor Necrosis Factor—Induced Death," 1993, Science, vol. 259.

Meikrantz et al., "Activation of Cyclin A–Dependent Protein Kinases During Apoptosis," 1994, Proc. Natl. Acad. Sci. USA, 91:3754–3758.

Plump et al., "Severe Hypercholesterolemia and Atherosclerosis in Apolipoprotein E–Deficient Mice Created by Homologous Recombination in ES Cells," 1992, Cell, 71:343–353.

Rothstein et al., "Chronic Inhibition of Superoxide Dismutase Produces Apoptotic Death of Spinal Neurons," 1994, Neurobiology, 91:4155–4159.

Schwartzman et al., "Apoptosis: The Biochemistry and Molecular Biology of Programmed Cell Death," 1993, Endocrine Reviews, 14(2):133.

Tsai et al., "Promotion of Vascular Smooth Muscle Cell Growth By Homocysteine: A Link To Atherosclerosis," 1994, Proc. Natl. Acad. Sci. USA, 91:6369–6973.

White, "Death–Defying Acts: A Meeting Review on Apoptosis," 1993, Genes & Development 7:2277–2284.

Williams et al., "Molecular Regulation of Apoptosis: Genetic Controls on Cell Death," 1993, Cell, 74:777–779.

Wyllie, "Death get a brake," 1994, Nature, vol. 369.

Zhang, et al., "Spontaneous Hypercholesterolemia and Arterial Lesions in Mice Lacking Apolipoprotein E," 1992, Science, 258:468–473.

Primary Examiner—Carlos Azpuru
Attorney, Agent, or Firm—Fish & Richardson P.C.

[57] ABSTRACT

A method of inhibiting arteriosclerosis or smooth muscle cell proliferation by identifying an animal having an artery suspected of needing such inhibition and contacting the artery with an apoptosis-inducing amount of an antioxidant.

16 Claims, 4 Drawing Sheets

ANTIOXIDANT-INDUCED APOPTOSIS IN VASCULAR SMOOTH MUSCLE CELLS

BACKGROUND OF THE INVENTION

This invention relates to prevention and treatment of arteriosclerosis.

Apoptosis or programmed cell death is characterized by cell shrinkage, membrane blebbing, and chromatin condensation that culminates in cell fragmentation (Kerr et al., 1972, Br. J. Cancer 26:239). Stimuli as diverse as hyperthermia, growth factor withdrawal, chemotherapeutic agents, radiation, and oxidative stress induce apoptosis in many cell types (Gerschenson et al., 1992, FASEB J. 6:2450; Schwartzman et al., 1993, Endocrine Reviews 14:133; Cohen, J., 1994, J. Lab. Clin. Med. 124:761). Antioxidants have been shown to prevent apoptosis in a number of cell types, such as lymphocytes (Hockenbery et al., 1993, Cell 75:421, Olivier et al., 1992, Abstract No. PoA 2376, Int. Conf. AIDS 8:A65; Roederer et al., 1993, Pharmacology 46:121; Sandstrom et al., 1994, J. Leukoc. Biol. 55:221), neurons (Rothstein et al., 1994, Proc. Natl. Acad. Sci. U.S.A. 91:4155), and vascular endothelial cells (Abello et al., 1994, Arch. Surg. 129:134,140).

SUMMARY OF THE INVENTION

The invention is based on the discovery that, unlike other cell types, vascular smooth muscle cells which contribute to the development of arteriosclerosis are induced to undergo apoptosis upon exposure to antioxidants. Accordingly, the invention features a method of inhibiting arteriosclerosis in an animal by identifying an animal, e.g., a human patient, having an artery suspected of needing such inhibition, and contacting the artery with an apoptosis-inducing amount of an antioxidant or mixture of antioxidants.

The antioxidant preferably contains a sulfur atom, e.g., 2-mercaptoethanol, dithiothreitol, glutathione, S-adenosylmethionine, dithiocarbamate, propylthiouracil, dimethylsulfoxide, cysteine, methionine, cysteamine, oxothiazolidinecarboxylate, timonacic acid, WR-2721, malotilate, 1,2-dithiol 3-thione, 1,3-dithiol 2-thione, lipoamide, sulfarlem, and oltipraz. More preferably, the sulfur is part of a sulfhydryl group; most preferably the antioxidant is N-acetylcysteine (NAC) or pyrrolidinedithiocarbamate (PDTC). Preferably, the antioxidant induces apoptosis in vascular smooth muscle cells, but does not induce apoptosis in vascular endothelial cells.

The invention also includes a method of inhibiting vascular smooth muscle cell proliferation, e.g., proliferation which may occur at the site of a vascular injury in an animal, by identifying an animal in need of such inhibition, and introducing an antioxidant into a blood vessel of the animal. Preferably the animal is a vertebrate, more preferably a mammal, and most preferably a human patient.

Smooth muscle cell proliferation in response to a vascular injury may occur as a consequence of balloon angioplasty, laser angioplasty, coronary artery surgery, atherectomy or coronary artery stent insertion. The antioxidant may be administered to the site of vascular injury or potential vascular injury systemically, e.g., by intravascular injection or oral delivery, or locally, e.g., during the invasive procedure. One means for accomplishing local delivery would be by providing the antioxidant on a surface of the vascular catheter, e.g., a balloon catheter coated with an antioxidant, which contacts the wall of the blood vessel.

Other features and advantages of the invention will be apparent from the following detailed description, and from the claims.

DETAILED DESCRIPTION

The drawings will first be briefly described.

Antioxidants

Figure 1:
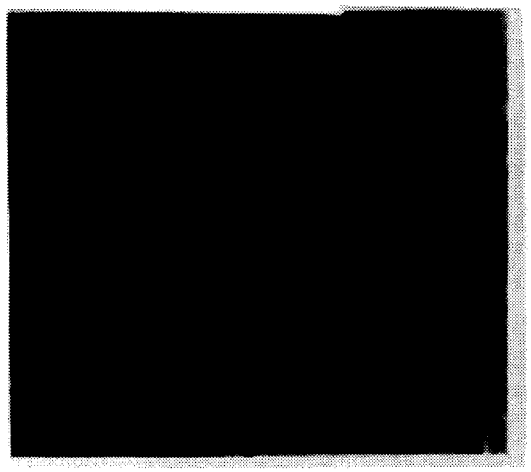
FIG. 1 is a light micrograph of proliferating rat aortic smooth muscle cells (RASMC) (100×).

Antioxidants have been shown to prevent apoptosis in many cell types, e.g., lymphocytes, neurons, and vascular endothelial cells. It has now been discovered that antioxidants, e.g., sulfur-containing antioxidants, e.g., those which contain a sulfhydryl group such as PDTC and NAC, induce apoptosis in vascular smooth muscle cells but not vascular endothelial cells or other cell types tested. In addition to PDTC and NAC, the class of sulfur-containing antioxidants includes for example, 2-mercaptoethanol, dithiothreitol, glutathione, S-adenosylmethionine, dithiocarbamate, propylthiouracil, dimethylsulfoxide, cysteine, methionine, cysteamine, oxo-thiazolidine-carboxylate, timonacic acid, WR-2721, malotilate, 1,2-dithiol 3-thione, 1,3-dithiol 2-thione, lipoamide, sulfarlem, and oltipraz. These and other sulfur-containing antioxidants, as well as antioxidants which do not contain sulfur, may be tested in vitro for apoptosis-inducing activity in vascular smooth muscle cells as described below, i.e., incubating vascular smooth muscle cells with the test compound and detecting apoptosis, e.g., by detecting DNA breaks or cell death. An increase in smooth muscle cell apoptosis in the presence of the test compound compared to that in the absence of the test compound indicates that the test compound induces apoptosis in vascular smooth muscle cells and is therefore likely to be useful in the methods of the invention. Antioxidants may also be tested in vivo using a mouse model of arteriosclerosis (Plump et al., 1992, Cell 71:343–353; Zhang et al., 1992, Science 258:468–471); antioxidants can be administered to an animal, e.g., systemically such as orally, intravenously, intraperitoneally, or locally such as during a surgical procedure, and the animal monitored for a decrease in arteriosclerosis or restenosis, e.g., by examining blood vessels for signs of apoptosis or a general decrease in size or incidence of arteriosclerotic lesions.

Microscopy

Morphology of RASMC was evaluated as follows. RASMC were harvested and cultured in Dulbecco's modified Eagle's medium (DMEM) containing 10% fetal calf serum as described (Tsai et al., 1994, Proc. Natl. Acad. Sci. U.S.A. 91:6369) and prepared for light microscopy using standard methods.

DNA fragmentation after PDTC-induced apoptosis in RASMC was evaluated as follows. After 6 hours of incubation with or without PDTC, RASMC were rinsed 3 times with phosphate-buffered saline (PBS), incubated in avidin (25 µg/ml in PBS and 0.4% Triton-X 100) for 30 minutes at room temperature to block endogenous biotin, rinsed three times with PBS, and then incubated in 3% $H_2O_2$ at room temperature for 10 minutes. After another three rinses with PBS the RASMC were rinsed with TdT and incubated in 50 µl TdT buffer (10 U TdT and 0.5 nmoles biotinylated dUTP) at 37° C. for 60 minutes. Biotinylated dUTP incorporated in DNA breaks in the nuclei was detected by an ABC (avidin-biotin complex) method (DAB/nickel chromogen). RASMC were counterstained with eosin.

For electron microscopy, RASMC were first treated with PDTC for 6 hours in 60-mm petri dishes. The cells were then processed for electron microscopy using standard methods, e.g., Meikrantz et al., 1994, Proc. Natl. Acad. Sci. U.S.A. 91:3754. RASMC were fixed in 2% glutaraldehyde in Dulbecco's phosphate-buffered saline for 30 minutes at room temperature, followed by further fixation with 1% osmium tetroxide in 0.1M cacodylate buffer for 30 minutes at room temperature.

Cell viability

To determine the viability of vascular cells after treatment with PDTC and NAC, subconfluent, exponentially growing RASMC, HASMC, and HAEC were incubated with PDTC or NAC in 24-well plates. After antioxidant treatment, cell viability was determined by a modified MTT assay. Conversion of the tetrazolium salt MTS [3-(4,5-dimethylthiazo-2-yl)-5-(3-carboxymethoxyphenyl)-2-(4-sulfophenyl)2-H-tetrazolium] by mitochondrial dehydrogenase to a formazan product (Buttke et al., 1993, J. Immunol. Meth. 157:233) was measured at an absorbance of 490 nm.

Protein Expression Studies

Protein overexpression was obtained by stable transfection of fetal RASMC (A7r5 cells, ATCC Designation No. CRL 1444) with a Bcl-2 expression plasmid (Tsujimoto, Y., 1989. Proc. Natl. Acad. Sci. U.S.A. 86:1958). Plasmid pCAj-bcl-2 (2.5 µg), containing the human Bcl-2 coding region and the neomycin resistance marker, and plasmid pCAj-SV2 (2.5 µg), which is identical to pCAj-bcl-2 but for the lack of a Bcl-2 coding region, were transfected into fetal RASMC by the Lipofectin® method (GIBCO/BRL, Gaithersburg, Md.). Clones were selected in medium containing G418 (Geneticin) (500 µg/ml).

For Western blot analysis, protein was extracted from cells transfected either with plasmid pCAj-SV2 (control) or pCAj-bcl-2, and 20 µg of protein was loaded in each lane of a polyacrylamide gel. After electrophoresis and transfer of proteins to a membrane, polyclonal antibody to human Bcl-2 (1:800 dilution, Pharmingen) was used to detect the Bcl-2 protein. Bcl-2 protein was detected as a 26-kDa band in the Bcl-2 lanes but not in the control lane.

Effect of antioxidants on vascular smooth muscle cells

Figure 2:
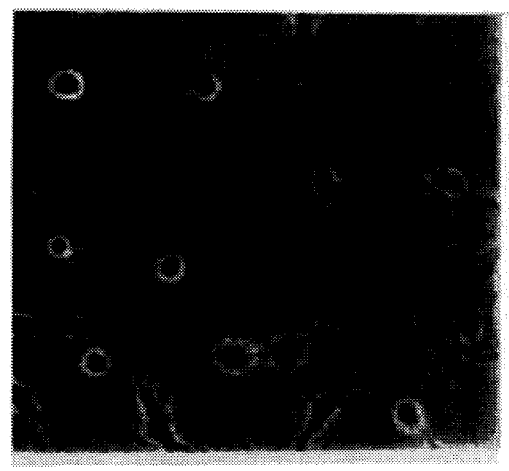
FIG. 2 is a light micrograph of proliferating RASMC after treatment with 150 mM PDTC (100×). After 6 hours of treatment, cytoplasmic condensation and cell shrinkage are visible in some RASMC. Arrow indicates a representative apoptotic cell.
Figure 3:
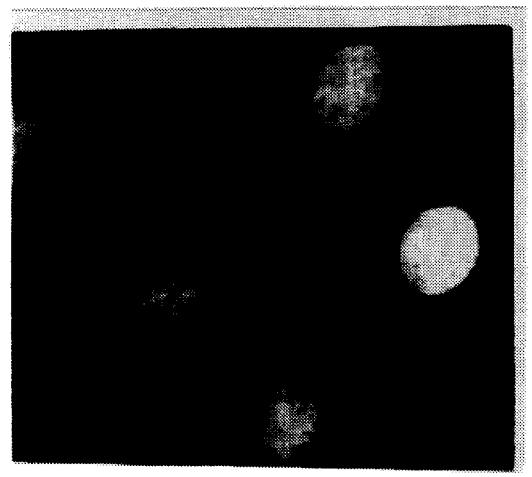
FIG. 3 is a micrograph of RASMC DNA stained with a fluorescent marker (600×). Cells were fixed in 4% paraformaldehyde at 4° C. for 15 minutes, and stained with Hoechst 33258 (8 µg/ml) for 10 minutes.
Figure 4:
FIG. 4 is a micrograph of RASMC DNA stained with a fluorescent marker (600×) after treatment with PDTC for 6 hours. Cells were fixed in 4% paraformaldehyde at 4° C. for 15 minutes, and stained with Hoechst 33258 (8 µg/ml) for 10 minutes. Arrow indicates an apoptotic body.

To test the effect of antioxidants, RASMC were treated with PDTC and NAC. After 6 hours of exposure to 150 mM PDTC, RASMC underwent cell shrinkage characteristic of apoptosis (see untreated RASMC in FIG. 1 compared to treated RASMC in FIG. 2). Fluorescent staining of the DNA revealed homogeneous, lightly stained nuclear chromatin in untreated cells shown in FIG. 3, compared to the chromatin condensation accompanying PDTC-induced apoptosis (see treated cells in FIG. 4).

Figure 5:
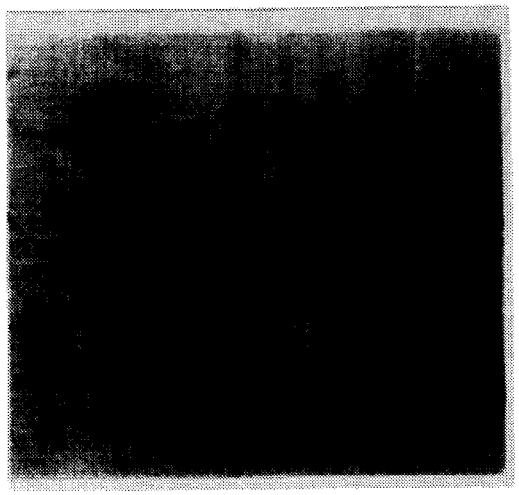
FIG. 5 is a micrograph of RASMC in which DNA breaks have been stained in situ by the TUNEL [terminal deoxynucleotidyl transferase (TdT)-mediated dUTP-biotin nick end labeling] method (200×).
Figure 6:
FIG. 6 is a micrograph of RASMC in which DNA breaks have been stained in situ by the TUNEL method after treatment with PDTC (200×). Arrow indicates a representative apoptotic nucleus.

DNA fragmentation by endonuclease is an indication of apoptosis. DNA breaks can be detected in situ by nick end labeling tissue sections with dUTP-biotin by terminal deoxynucleotidyl transferase. In contrast with untreated cells (shown in FIG. 5), positive staining was visible in most of the nuclei in RASMC that had been treated with PDTC (see FIG. 6).

Figure 7:
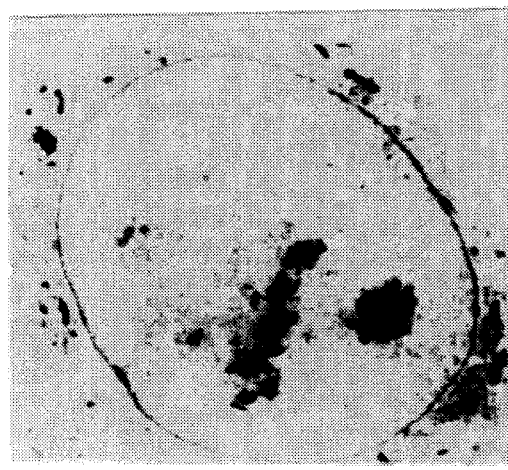
FIG. 7 is an electron micrograph of RASMC (3000×) showing a large nucleolus and scanty heterochromatin.
Figure 8:
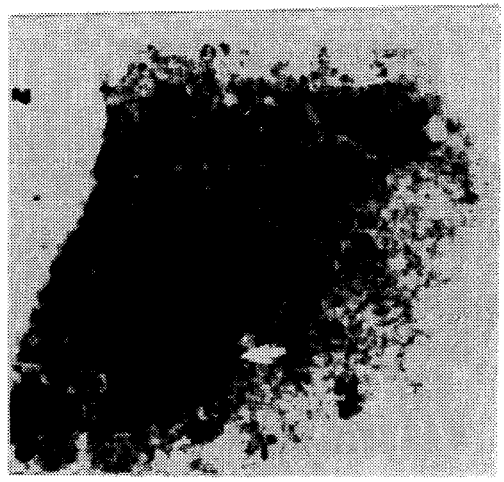
FIG. 8 is an electron micrograph of RASMC (3000×) after treatment with PDTC showing marked chromatin condensation within an intact nuclear envelope. Arrow marks dense aggregation of chromatin in the periphery of the nucleus.

Electron microscopy experiments revealed that highly condensed chromatin localized to the inner side of an intact nuclear membrane in PDTC-treated RASMC (see an antioxidant-treated nucleus shown in FIG. 8 compared to an untreated nucleus in FIG. 7). RASMC treated with 10 mM NAC manifested morphologic changes identical to those observed in PDTC-treated RASMC (not shown), indicating that two different antioxidants induce apoptosis in vascular smooth muscle cells. The antioxidant α-tocopherol was found not to induce apoptosis in vascular smooth muscle cells.

Figure 9:
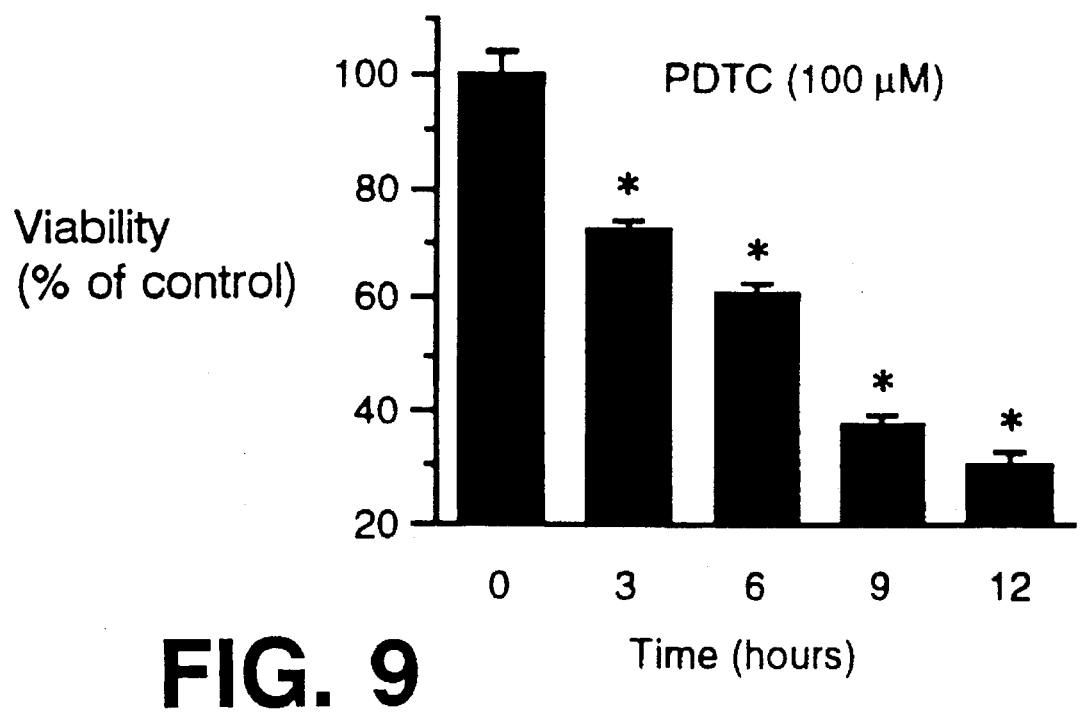
FIG. 9 is a bar graph showing a time course of the effect of PDTC on RASMC viability.
Figure 10:
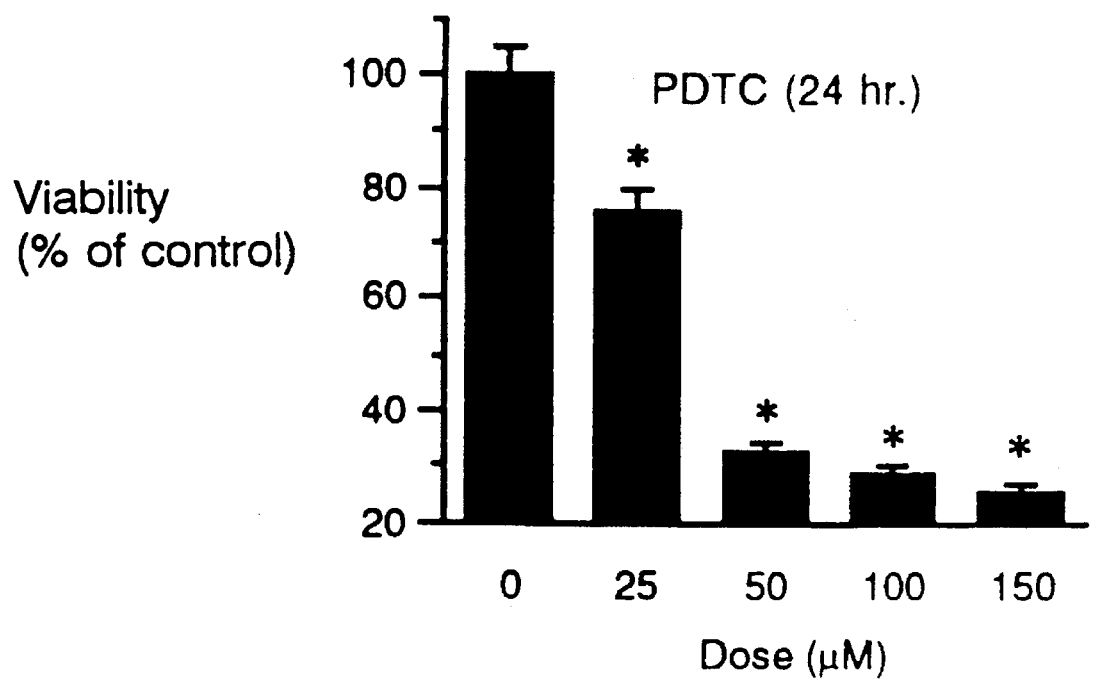
FIG. 10 is a bar graph showing a dose response of the effect of PDTC on RASMC viability.
Figure 11:
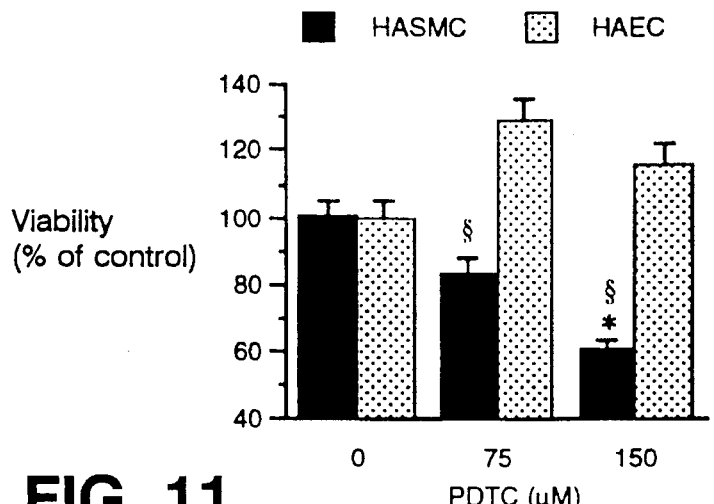
FIG. 11 is a bar graph showing the differential effect of PDTC on the viability of human aortic smooth muscle cells (HASMC) and human aortic endothelial cells (HAEC).
Figure 12:
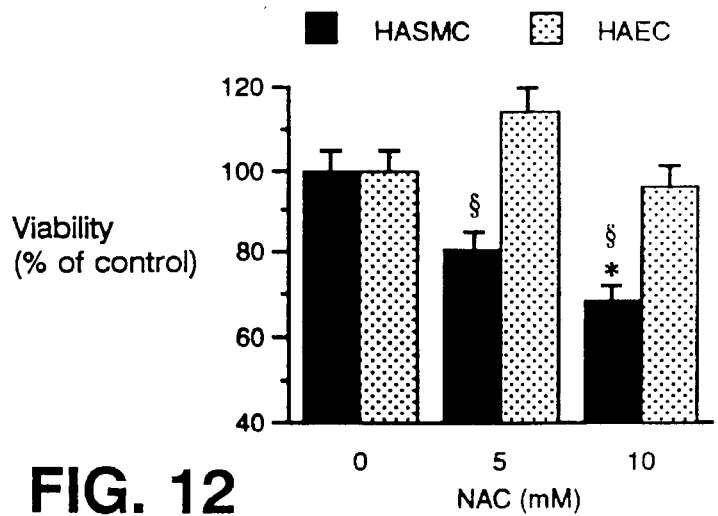
FIG. 12 is a bar graph showing the differential effect of NAC on the viability of HASMC and HAEC. Plotted values in FIGS. 9–12 represent mean ±SE from 4 samples. A factorial analysis of variance was applied to the values, followed by Fisher's least significant difference test. Significance was accepted at $p<0.05$. "*" indicates that the treated group is significantly different from the control group. "§" indicates that the HASMC group is significantly different from the HAEC group.

Antioxidant-induced apoptosis was also measured using a modified MTT assay of cell viability. The viability of RASMC decreased within 3 hours of treatment with PDTC (FIG. 9) and was reduced to approximately 30% at 12 hours. PDTC also decreased the viability of RASMC in a dose-dependent manner (FIG. 10). As little as 25 mM PDTC reduced RASMC survival by 25%, whereas 150 mM PDTC reduced survival by 73%. This decrease in cell survival was not limited to RASMC: PDTC (FIG. 11) and NAC (FIG. 12) both caused dose-dependent reductions in survival in HASMC as well. In contrast, neither PDTC nor NAC reduced survival in HAEC (FIGS. 11–12). The concentrations of NAC that induced apoptosis in vascular smooth muscle cells (FIG. 12) have been shown to prevent apoptosis in other cell types, such as lymphocytes, neurons, and endothelial cells (Hockenbery et al.,1993, Cell 75:421, Olivier et al., 1992, (Abstract No. PoA 2376), Int. Conf. AIDS 8:A65; Roederer et al., 1993, Pharmacology 46:121; Sandstrom et al., 1994, J. Leukoc. Biol. 55:221), neurons (Rothstein et al., 1994, Proc. Natl. Acad. Sci. U.S.A. 91:4155), and vascular endothelial cells (Abello et al., 1994, Arch. Surg. 129:134,140). Thus, it is possible that the induction of apoptosis by antioxidants is unique to vascular smooth muscle cells.

Figure 13:
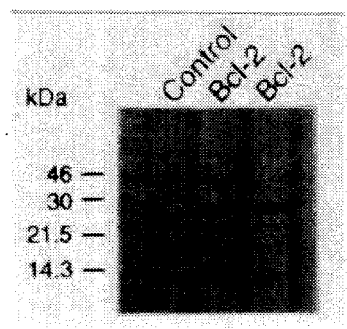
FIG. 13 is a photograph of a Western blot showing Bcl-2 protein expression.
Figure 14:
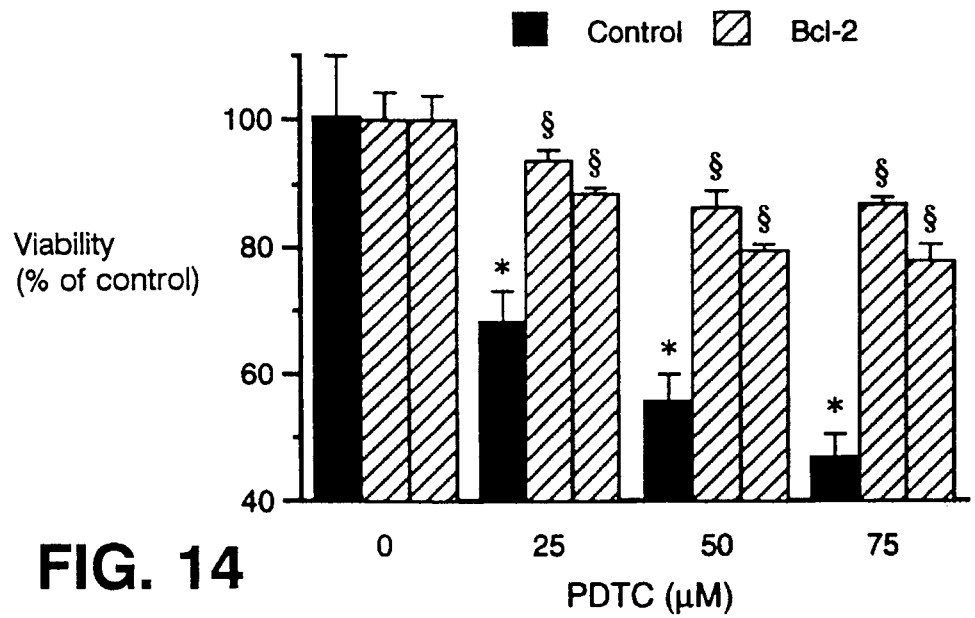
FIG. 14 is a bar graph showing viability of control and Bcl-2 cell lines exposed to PDTC. Fetal RASMC were treated with 25 to 75 µM PDTC for 24 hours, and viability was determined by the MTT [3-(4,5-dimethylthiozol-2-yl)-2,5-diphenyl tetrazolium bromide] assay. PDTC reduced the viability of control RASMC (black bars) in a dose-dependent manner. Viability in the two lines of RASMC that overexpressed Bcl-2 (hatched bars) was significantly greater than that in the control line. "*" indicates P<0.05 (treated group versus control). "§" indicates P<0.05 (Bcl-2 groups versus control).

To determine whether Bcl-2 inhibited antioxidant-induced apoptosis in vascular smooth muscle cells, expression plasmids containing the human Bcl-2 coding region (control plasmids did not contain the human Bcl-2 coding region) were transfected into fetal RASMC. Several stably-transfected clones were isolated, and Bcl-2 expression was confirmed by Western blotting with an antibody against human Bcl-2 (FIG. 13). As in adult RASMC (FIG. 9), PDTC (FIG. 14) and NAC (not shown) both induced dose-dependent apoptosis in fetal RASMC. However, apoptosis was found not to be induced by either PDTC (FIG. 14) or NAC (data not shown) in cells that overexpressed Bcl-2. These data indicate that Bcl-2 overexpression rescues RASMC from apoptosis induced by PDTC and NAC, and suggests that Bcl-2 prevents apoptosis in vascular smooth muscle cells through a pathway unrelated to its antioxidant activity. The unique susceptibility to antioxidants of vascular smooth muscle cells indicates that they respond differently than other cell types to changes in the reduction-oxidation state.

Use

The discovery that antioxidants promote apoptosis in vascular smooth muscle cells, but not in vascular endothelial cells, is the basis of the inventive methods to treat arteriosclerosis and vascular injury. Proliferation of vascular smooth muscle cells is one of the most prominent features of arteriosclerotic lesions, particularly in restenosis after balloon angioplasty.

An animal, e.g., a human patient, with arteriosclerosis or at risk of developing arteriosclerosis (and therefore in need of inhibition of arteriosclerosis or inhibition of smooth muscle cell proliferation) may be identified using standard medical procedures, such as angiographic visualization of the lumen of a blood vessel, Doppler probes for measuring velocity and volume of blood flow, stress test, and ultrasound to detect arteriosclerotic plaques. Other patients in need of inhibition of arteriosclerosis or vascular smooth muscle cell proliferation according to the invention are those with angina or stroke. Improvement of the patient's condition during and after therapy may be similarly monitored. Patients undergoing invasive vascular procedures are also at risk for developing arteriosclerosis, in particular restenosis after balloon angioplasty.

Angioplasty, used to treat arteriosclerosis, involves the insertion of catheters, e.g., balloon catheters, through an occluded region of a blood vessel in order to expand it. However, aftermath of angioplasty may be problematic. Restenosis, or closing of the vessel, can occur as a consequence of injury, e.g., mechanical abrasion associated with the angioplasty treatment. This restenosis is believed to be caused by proliferation of smooth muscle cells stimulated by vascular injury. Other anatomical disruptions or a mechanical disturbances of a blood vessel, e.g., laser angioplasty, coronary artery surgery, atherectomy and coronary artery stents, may also cause vascular injury and subsequent proliferation of smooth muscle cells.

Induction of apoptosis in proliferating smooth muscle cells in arteriosclerotic lesions by antioxidants is likely to be an effective treatment for arteriosclerosis. Antioxidants can be administered to patients parenterally, e.g., intravenously, subcutaneously, intramuscularly, and intraperitoneally. Many of these agents may also be administered orally. Sustained release administration such as depot injections or erodible implants may also be used. The compounds may also be directly applied during surgery. In addition to administration after arteriosclerosis or vascular injury has occurred, antioxidants may administered to patients prior to detection of arteriosclerosis, e.g., to patients at risk of developing arteriosclerosis. According to the invention, antioxidants may be administered in pharmaceutically acceptable carriers, i.e., biologically compatible vehicles which are suitable for administration to an animal e.g., physiological saline. A therapeutically effective amount of antioxidant is an amount which is capable of producing a medically desirable result, e.g., apoptosis in vascular smooth muscle cells, in a treated animal. Such an amount can be determined by one of ordinary skill in the art. As is well known in the medical arts, dosage for any given patient depends upon many factors, including the patient's size, body surface area, age, the particular compound to be administered, sex, time and route of administration, general health, severity of arteriosclerosis or vascular injury, and other drugs being administered concurrently.

Antioxidants may be administered in a variety of forms. These include, for example, solid, semi-solid, and liquid dosage forms, such as tablets, pills, powders, liquid solutions or suspensions, liposomes, injectable and infusible solutions. The preferred form depends on the intended mode of administration and therapeutic application. Antioxidants may be administered in pharmaceutically acceptable carriers which are known to those of skill in the art. Typically, the compositions of the invention are in the form of a unit dose and which can be administered to the patient one or more times a day. The methods of this invention may be used in combination with other therapies to treat arteriosclerosis.

Once improvement of the patient's condition has occurred, a maintenance dose may be administered if necessary. Subsequently, the dosage or the frequency of administration, or both, may be reduced, as a function of the symptoms, to a level at which the improved condition is retained. When the symptoms have been alleviated to the desired level, treatment may cease. Patients may, however, require intermittent treatment on a long-term basis upon any recurrence of disease symptoms.

Other Embodiments

Antioxidants which induce apoptosis in vascular smooth muscle cells may also be used to treat or prevent transplant arteriosclerosis. Antioxidant compounds may be tested for in vivo efficacy using a mouse model for transplant arteriosclerosis (Shi et al., 1994, Cir. Res. 75:199–207). For treatment of transplant arteriosclerosis, antioxidants may be administered to the animal as described above, immediately before and during the transplant procedure, and for an extended period of time afterward. In addition, the donor organ may be soaked in or perfused with an antioxidant prior to transplantation into the host animal.

Other embodiments are within the following claims.

What is claimed is:

1. A method of inhibiting arteriosclerosis in an animal, comprising identifying an animal having an artery suspected of needing said inhibition and contacting said artery with an apoptosis-inducing amount of an antioxidant.

2. The method of claim 1, wherein said animal is a human.

3. The method of claim 1, wherein said antioxidant is a sulfur-containing antioxidant.

4. The method of claim 3, wherein said antioxidant comprises a sulfhydryl group.

5. The method of claim 3, wherein said antioxidant is N-acetylcysteine.

6. The method of claim 3, wherein said antioxidant is pyrrolidinedithiocarbamate.

7. The method of claim 3, wherein said antioxidant is chosen from the group consisting of 2-mercaptoethanol, dithiothreitol, glutathione, S-adenosylmethionine, dithiocarbamate, propylthiouracil, dimethylsulfoxide, cysteine, methionine, cysteamine, oxo-thiazolidinecarboxylate, timonacic acid, WR-2721, malotilate, 1,2-dithiol 3-thione, 1,3-dithiol 2-thione, lipoamide, sulfarlem, and oltipraz.

8. The method of claim 3, wherein said antioxidant is a mixture of two or more antioxidants.

9. The method of claim 8, wherein said mixture comprises N-acetylcysteine and pyrrolidinedithiocarbamate.

10. A method of inhibiting vascular smooth muscle cell proliferation in an animal, comprising identifying an animal in need of said inhibition, and introducing an antioxidant into a blood vessel of said animal.

11. The method of claim 10, wherein said animal is a human.

12. The method of claim 10, wherein said proliferation occurs at the site of vascular injury.

13. The method of claim 10, wherein said antioxidant is a sulfur-containing antioxidant.

14. The method of claim 13, wherein said antioxidant comprises a sulfhydryl group.

15. The method of claim 13, wherein said antioxidant is N-acetylcysteine.

16. The method of claim 13, wherein said antioxidant is pyrrolidinedithiocarbamate.

* * * * *